(12) United States Patent
Hogrel

(10) Patent No.: US 9,857,261 B2
(45) Date of Patent: Jan. 2, 2018

(54) SYSTEM FOR MEASURING A PALMAR GRIPPING FORCE

(71) Applicant: INSTITUT DE MYOLOGIE, Paris (FR)

(72) Inventor: Jean-Yves Hogrel, Montrouge (FR)

(73) Assignee: INSTITUT DE MYOLOGIE, Paris (FR)

(*) Notice: Subject to any disclaimer, the term of this patent is extended or adjusted under 35 U.S.C. 154(b) by 207 days.

(21) Appl. No.: 14/389,333

(22) PCT Filed: Mar. 29, 2013

(86) PCT No.: PCT/FR2013/050694
§ 371 (c)(1),
(2) Date: Sep. 29, 2014

(87) PCT Pub. No.: WO2013/144523
PCT Pub. Date: Oct. 3, 2013

(65) Prior Publication Data
US 2015/0047412 A1 Feb. 19, 2015

(30) Foreign Application Priority Data
Mar. 30, 2012 (FR) ...................................... 12 52928

(51) Int. Cl.
*G01L 25/00* (2006.01)
*A61B 5/22* (2006.01)
*G01D 3/02* (2006.01)

(52) U.S. Cl.
CPC .............. *G01L 25/00* (2013.01); *A61B 5/225* (2013.01); *A61B 2560/0223* (2013.01); *G01D 3/022* (2013.01)

(58) Field of Classification Search
CPC ............ A61B 5/225; A61B 2560/0223; G01D 3/022; G01L 25/00

(Continued)

(56) References Cited

U.S. PATENT DOCUMENTS 3,442,132 A * 5/1969 De Mare .................. A61B 5/00
482/49
3,672,219 A * 6/1972 Van Patten .............. A61B 5/22
482/49

(Continued)

FOREIGN PATENT DOCUMENTS

| CN | 1701758 | * 11/2005 |
| JP | 1-94826 | * 4/1989 |
| JP | 9-313467 | * 12/1997 |

OTHER PUBLICATIONS

International Search Report of PCT/FR2013/050694 dated Jun. 10, 2013.

*Primary Examiner* — Daniel S Larkin
(74) *Attorney, Agent, or Firm* — Amster, Rothstein & Ebenstein LLP

(57) ABSTRACT

The invention relates to a system for measuring a palmar gripping force, comprising a device (1) for measuring said palmar gripping force, which device comprises: a handle configured to receive a palmar gripping force; a force sensor (3); and an electronic module (6) integrated into the device and comprising at least one microcontroller (61) connected to the sensor (3) and able to process data originating from said sensor (3), characterized in that the force sensor comprises a stress gauge with a minimum precision of 50 g; a controlling system is also provided and comprises means able to do the following: calibrate the sensor using a linear calibration curve; and transmit the sensor measurements to a display unit (8) and/or a storage unit and/or a processing unit, preferably via wired or wireless means.

10 Claims, 3 Drawing Sheets

(58) Field of Classification Search
USPC .................. 73/1.15, 379.01, 379.02, 379.09
See application file for complete search history.

(56) References Cited

U.S. PATENT DOCUMENTS

| | | | |
|---|---|---|---|
| 4,939,933 A * | 7/1990 | Curran | ................... A61B 5/103 482/8 |
| 5,014,229 A | 5/1991 | Mofachern | |
| 5,398,696 A | 3/1995 | Wiley | |
| 5,904,639 A | 5/1999 | Smyser et al. | |
| 2002/0132655 A1 | 9/2002 | Mercer et al. | |

* cited by examiner

SYSTEM FOR MEASURING A PALMAR GRIPPING FORCE

TECHNICAL FIELD OF THE INVENTION

The invention relates to the field of methods and devices for measuring palmar gripping force to assess the integrity of muscular control and effectors, in particular of the forearm and hand of an individual.

The invention therefore forms part of the field of metrology; it makes it possible to measure forces.

During the muscular functional assessment of an individual, the palmar gripping force is one of the most interesting functions since it constitutes a good indicator of the overall muscular capacity, the nutritional status, the autonomy and in general the health of the individual.

Devices are known that make it possible to quantify a pathological or post-traumatic state and to validate the effect of treatment on the neuromuscular system, in particular in re-education.

In this context, a need has developed for patients suffering for example from neuromuscular pathologies and whose palmar gripping force is sometimes very weak. At these levels of forces, it is important for the measuring device to be sufficiently sensitive and precise to reliably assess the palmar gripping force of the patient. It is a case of measuring in order to monitor the changes in forces developed by very weak patients.

Moreover, it is important for the measuring devices also to make it possible to measure the palmar gripping force of persons in good health, and sportspersons.

PRIOR ART

In a clinical environment, assessment of palmar gripping is effected by means of manual tests, for example by a physiotherapist. It is known that such manual tests do not provide the precision necessary for rigorous monitoring, in particular in the context of therapeutic tests.

The prior art proposes measuring devices equipped with sensors. In general, these devices do not make it possible to measure a wide range of forces with precision and are not sensitive to the small forces generated by the weakest patients.

A first group of grips are for example known, comprising mechanical ergometers where the response of the sensors is determined by the deformation of a spring or a metal blade. The measurements are usually read by means of a needle on a dial or by means of a digital display when a strain gauge is used to convert the deformation of the mechanical part into electrical voltage. The drawbacks of such ergometers lie in the lack of precision, in particular in needle ergometers. Furthermore, it is difficult to record forces at given intensities since the type of display is not suitable. This is because the majority of these ergometers retain only the maximum gripping value.

A second group of grips is known, comprising hydraulic ergometers where the grip contains a fluid, the compression of which causes the deformation of a membrane. The display is provided by a needle dial or a digital dial. Just as with mechanical grips, it is often difficult to require a subject to maintain a given level of force, so that the measurements are difficult to make.

Another group of grips includes electronic systems that can be connected to a data processing module such as a computer. The main drawback of the latter group lies in high prices, in particular because of the use of a card for acquiring processing data issuing from the sensor used. This is because, in order to obtain precise and reliable measurements, the data acquisition and processing effected by said card are based on complex processes that involve long computing times, a high consumption of energy and multiple and/or expensive components. Furthermore, the very great majority of current electronic systems are provided with cabled communication means, which has the drawback of being impractical when the patient is in a wheelchair or immobilised on a bed for example.

Furthermore, the sensitivity and precision of existing systems may prove to be insufficient for the weakest patients.

Other devices comprise sensors associated with a calibration method implemented by computer programs.

Thus, through the document WO 2011/044520, a system, method and apparatus are known for performing isometric exercises for diagnostic purposes or therapeutic purposes. The apparatus disclosed comprises a communication port external to a computer making it possible in particular to program it. The apparatus comprises load sensors and electronic amplification means associated with an analogue to digital converter. This document also discloses a calibration of the apparatus by nineteen combinations of six standard masses correlated with a calculation of the mean quadratic error type.

This type of system is however not optimum since it comprises a calibration based on a complex calculation which gives rise to long computing times and expensive computing means.

DISCLOSURE OF THE INVENTION

The invention aims to remedy the drawbacks of the prior art and in particular to propose a system for measuring a palmar gripping force, comprising a device for measuring said palmar gripping force that comprises a grip configured so as to receive a palmar griping force,
a force sensor configured so as to measure said palmar gripping force, and
an electronic module integrated in the device and comprising at least one microcontroller connected to the sensor and able to process data issuing from said sensor.

According to a first advantageous aspect, the system comprising a strain gauge able to detect forces from a zero or almost zero value, and which has a precision at a minimum of approximately 50 g for a range of measurements ranging from 0 to 90 kg, and which has a precision at a minimum of approximately 50 g and/or a sensitivity of less than approximately 10 g.

According to another advantageous aspect, the electronic module comprises means suitable for performing the following actions:

(a)—calibrating the sensor, in which:
(a1)—the sensor receives a plurality of calibration forces, and
(a2)—establishing a linear calibration function from calibration points, a first coordinate of which is a sensor measurement and a second coordinate of which is the value of said calibration force, said calibration function being linear by segments, and
(b)—recording a palmar gripping force value according to a first coordinate of a point of the linear calibration function, and determining a calibrated force value corresponding to the second coordinate of said point of the linear calibration function.

Thus the measuring system according to the invention has a highly advantageous sensitivity never reached by the prior art. Furthermore, this system can be adapted to a wide range of measurements, and hence a large number of possible applications, from musculo-deficient persons to high-level sportspersons.

Preferably, the calibration of the sensor is carried out on at least three calibration measurements.

Advantageously, the electronic module also comprises means of transmitting said calibrated force value to a display unit and/or a storage unit and/or a data processing unit.

Preferably, the display unit and/or the storage unit and/or the processing unit are provided in the electronic module of the measuring device.

Thus the system according to the invention affords measurements that are improved from the point of view of precision both for patients with very weak muscular capabilities and for persons in good health or high-level sportspersons.

Furthermore, the resolution is improved significantly in such a measuring system. In particular, a resolution of around 10 g can be achieved.

Thus it is possible to calibrate the sensor by means of a simplified function. Such a computing simplification makes it possible to use less complex microcontrollers than those of the prior art. The result is a significant reduction in costs and expenditure in energy. Furthermore, small microcontrollers can be used.

According to a preferred variant, the display unit and/or the storage unit and/or the processing unit and/or the signal transmission unit are provided in a specific module connected to said electronic module of the measuring device, said transmission being wired and/or wireless.

For example, the display and/or storage of the data is performed on a computer, which makes it possible to provide scientific and/or games software for the acquisition and display of the measured signals. This feature makes it possible to imagine a large number of different assessment, re-education or training protocols.

Preferentially, the sensor is calibrated on at least three calibration measurements.

Advantageously, the grip of the measuring device comprises an external frame formed from several elements, and at least one internal bar parallel to a first element of the external frame and able to move in translation vis-à-vis the first element of the external frame; the force sensor is configured so as to measure a force associated with said translation.

According to a variant, the handle comprises a means for adjusting an initial separation between the movable internal bar and the first element of the external frame.

Preferably, the measuring system comprises means for selecting an operating mode chosen from:
 a so-called measuring mode for said measurement of a palmar gripping force, or
 a so-called calibration mode for implementing said calibration.

According to an advantageous aspect, the measuring system comprises means of wired and/or wireless connection to a control unit.

Another subject matter of the invention consists of a computer program product that can be loaded into a memory of a computer and/or the microcontroller of the electronic module, comprising software code parts for performing calibration and measurement steps of a system for measuring palmar gripping force as described previously.

BRIEF DESCRIPTION OF THE FIGURES

Other features, details and advantages of the invention will emerge from a reading of the following description, with reference to the accompanying figures, which illustrate.

For more clarity, identical and similar elements are marked by identical reference signs on all the figures.

DETAILED DESCRIPTION OF EMBODIMENTS

Figure 1A:
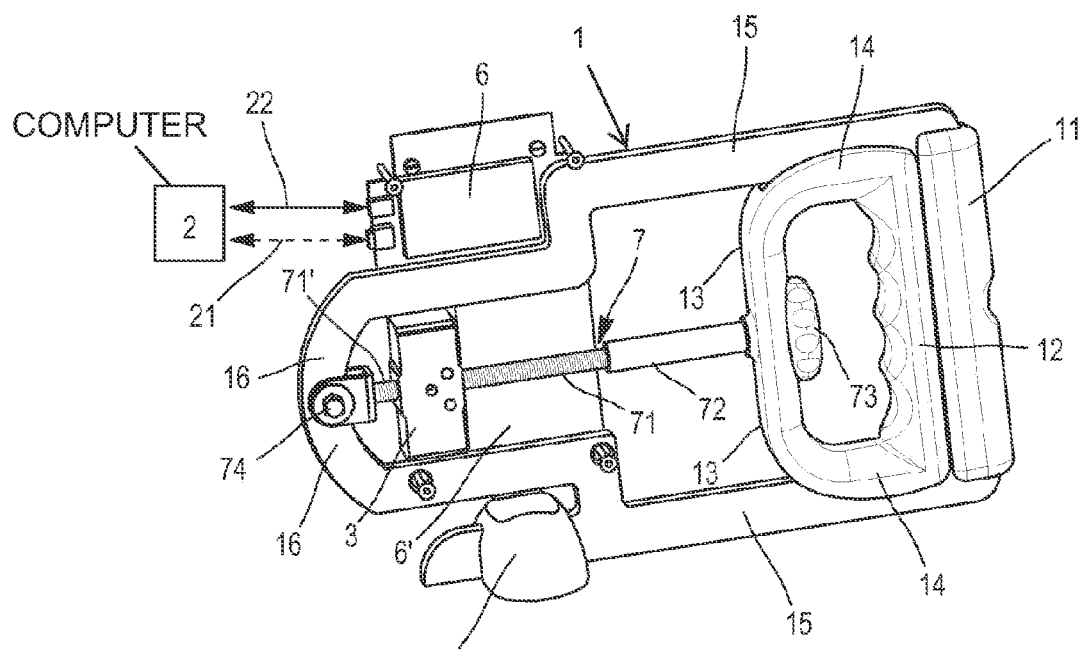
FIGS. 1A and 1B illustrate a device according to a first variant of the invention configured for a system according to the invention.
Figure 1B:
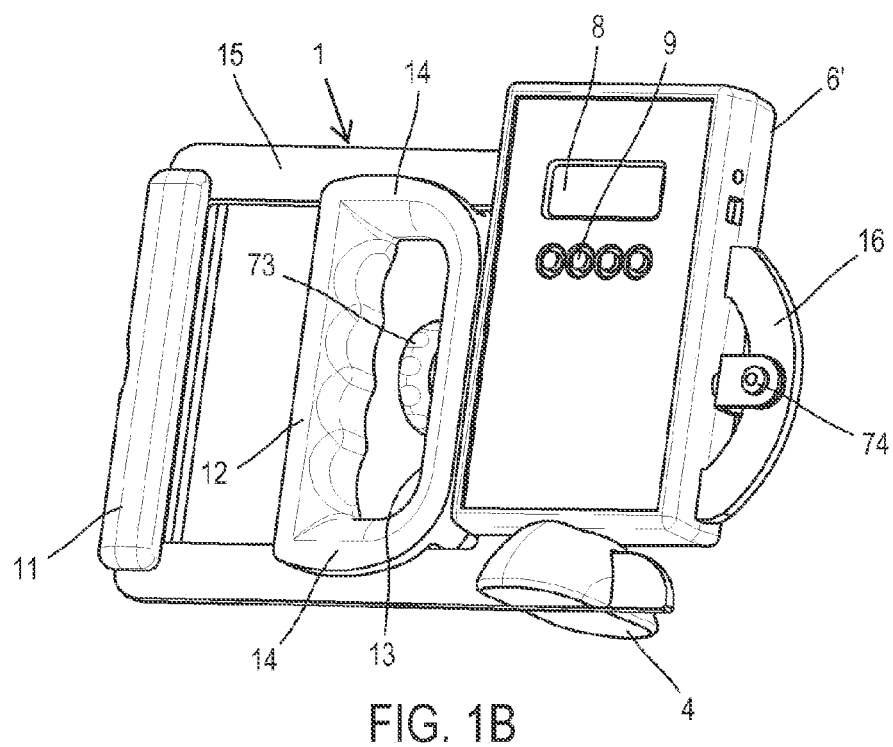

According to the representations in FIGS. 1A and 1B, the device 1 according to a first variant of the invention comprises an external frame formed by two lateral bars 15 and a top bar 11. The device also comprises an internal frame formed by two guided juxtaposed lateral bars 14 parallel to the lateral bars 15; a top bar 12 is disposed parallel to the top bar 11. The internal frame also comprises a bottom bar 13. The internal frame 12, 13, 14 has roughly a rectangular shape; the top bar 12 will be gripped by the hand of the user, who will simultaneously hold the top bar 11. The internal frame may be in a single piece, obtained for example by plastic injection moulding.

Furthermore, optionally, a lateral bar 15 of the external frame may comprise a foot 4 for placing the grip on a flat surface.

An electronic circuit 6' comprising an electronic module is fixed to the external frame. A sensor 3 consisting of a high-precision strain gauge is disposed against the electronic circuit 6' and is attached by a spindle 7 parallel to the lateral bars 15 and itself fixed to the bottom bar 13 of the internal frame. Thus, this sensor 3 is secured to the internal frame and is connected to an electronic module 6. As will be explained below, this arrangement makes it possible to measure the forces related to the movements of the top bar 12 of the internal frame towards the top bar 11 of the external frame.

The grip also comprises a means for adjusting the opening of the grip, in particular the initial separation between the top bars 11 and 12 held and actuated by the user. This adjustment means consists here of a threaded spindle 71 cooperating with a tapped part 72 (the combination of the threaded spindle 71 and the tapped part 72 together form the general spindle structure designated by reference number 7). The threaded spindle 71 is screwed onto the sensor 3 on a first face, while the tapped part 72 is fixed to the internal frame 12, 13, 14. An adjustment wheel 73 is provided here at the bottom bar 13 in order to adjust the initial separation between the internal frame and the external frame. FIG. 1A shows the internal frame in contact with the external frame while FIG. 1E shows the internal frame in the position away from the external frame. A second spindle 71' aligned with the spindle 71 is attached to the other side of the sensor.

For more stability and better balancing of the forces, the spindle 7 of the grip, in particular the threaded internal spindle 71, is fixed to the external frame at the middle of a bar 16 opposite to the top bar 11. A fixing means 74, consisting here of a pivot screw system, allows free movement of the spindle 71' of the sensor 3.

The sensor used is a Low Height Load Cell SML sensor marketed by the company Interface Inc. The preferred sensor has a nominal capacity of approximately 89 kgf (200 lbf).

Referring to FIG. 1B, the electronic circuit 6', the sensor 3 and part of the threaded internal spindle 71 are housed in a box that has keys 9 and a screen, for example of the LCD type 8. The keys 9 serve for example to put the device in calibration mode or in measurement mode and the display 8 makes it possible to view directly the forces measured. Thus, this variant may be used autonomously, that is to say without any connection to a computer or any other data storage and processing device.

Figure 2:
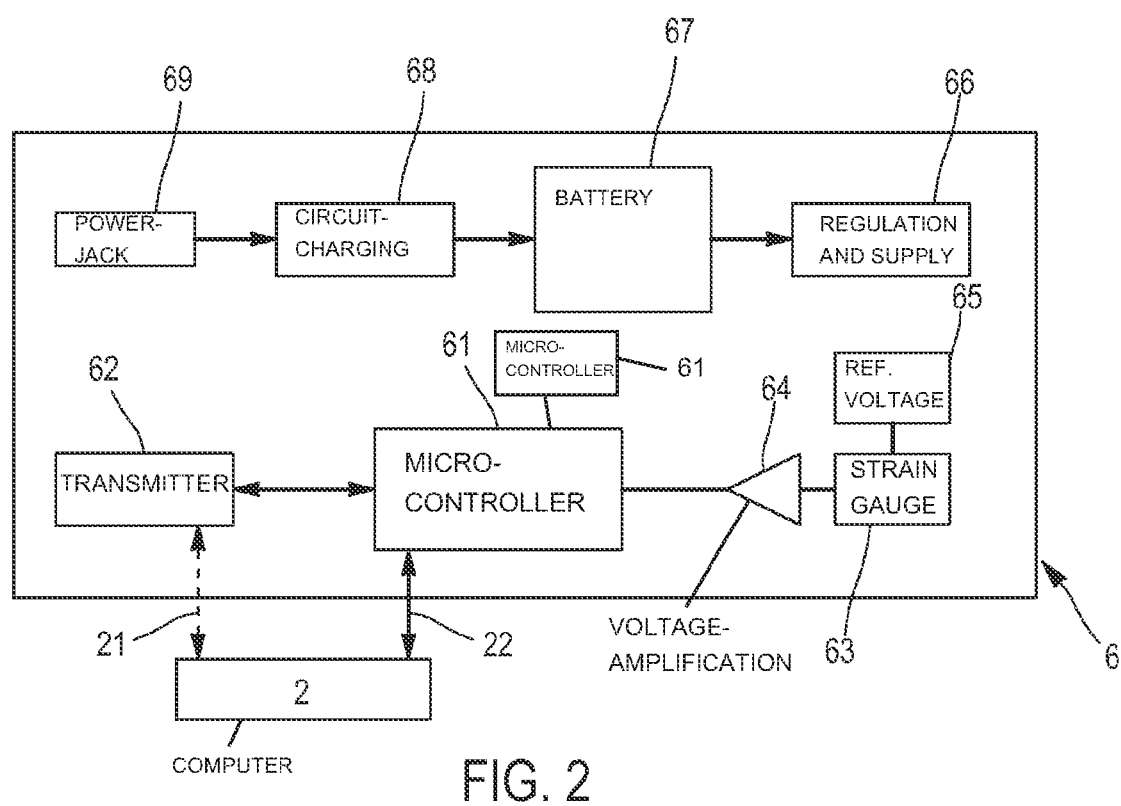
FIG. 2 shows a diagram of the electronic module for a device according to the invention.

As illustrated in FIG. 2, the electronic module 6 can be connected to a computer 2. Wired connection means 22—such as an RS 232 cable, can be used for this purpose. Wireless connection means 21, such as a radio-frequency transmitter 62, are preferably used. Thus, the device according to the invention can cooperate with a computer program implementing the display and processing of the information received from said force sensor 3. A games interface can be implemented without departing from the scope of the invention.

Referring to FIG. 2, the electronic module 6 comprises in particular sub-modules 66, 67 intended for the electrical supply and recharging of the device. By way of illustration, a so-called "power jack" sub-module 69 for connection to an external current supply source to the device 1, a circuit-charging sub-module 68, a battery sub-module 67 and a regulation and supply sub-module 66 can be seen in FIG. 2.

The electronic module 6 also comprises sub-modules such as: a so-called "Ref. voltage" sub-module 65 intended to fix a reference voltage of the measurements; a strain gauge sub-module 63; a voltage-amplification sub-module 64; a microcontroller sub-module 61.

The microcontroller 61 advantageously comprises an EPROM.

The microcontroller 61 can be connected to the computer 2 by a wired connection 22 by means of a serial port. The transmitter 62 also makes it possible to send information for example to the computer 2, as represented by the reference 21 (wireless connection).

The microcontroller module 61 integrates several components and in particular a RAM, a FLASH memory and an analogue to digital converter. These components are configured so as to allow a calibration of the measurements of the forces applied to the strain gauge 63 by means of the sensor 3 of the device according to the invention. For this purpose, a computer program is loaded into the memory of the microcontroller 61 so as to effect said calibration and said measurements according to a given method.

The preferably wireless connection to a computer has a particular advantage in the use of the grip. For example, software can be installed on a computer (in combination with a suitable wireless receiver), which makes it possible to view in real time the acquisition of the forces measured, and the comparison with measurements already acquired, etc. The patient or the sportsperson tested can thus monitor his progress in real time. Thus, during tests, the attention of the patient is focused on these illustrations, which is advantageous during assessment tests, in particular with children.

Furthermore, the use of such software makes it possible to ensure better monitoring of the measurements to produce statistics more easily, and thus to go further in the analysis of the data.

Figure 3:
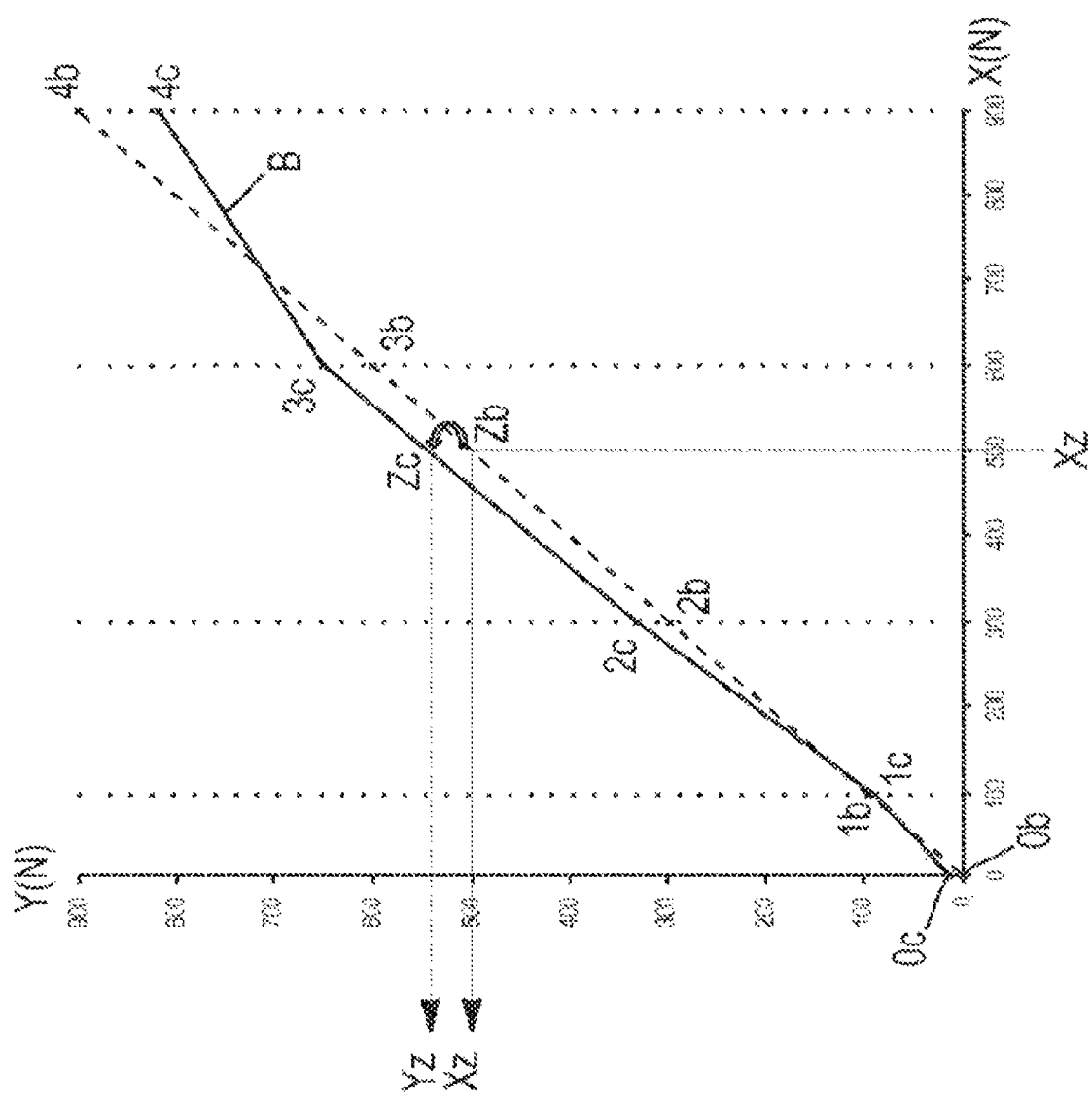
FIG. 3 shows a graphical representation of the calibration of the sensor.

FIG. 3 illustrates the calibration of the sensor 3 in the system according to the invention. Naturally, the purpose of the graphical illustration is to explain the calculations made by the measuring system. As can be seen in this figure, five raw measurements have been made at 0, 100, 300, 600 and 900 N. The distribution of the raw measurements on the reference frame in FIG. 3 is represented by the calibration curve B in a solid line. Each calibration point $0c$ to $4c$ is produced by associating on the abscissa X the raw measurement $X0$ to $X4$ of the sensor and on the ordinate Y the real value $Y0$ to $Y4$ of the corresponding calibration force. The raw measurement points $0b$ to $4b$ have the same abscissa and the same ordinate, corresponding to the raw measurement (without calibration).

Thus, in order to compensate for linearity faults in the sensor, it is possible to define a calibration curve that makes it possible to display on the grip a corrected measurement $Y_Z$ of the raw measurement $X_Z$ recorded by the sensor.

It is advantageous to emphasise that the calibration is carried out by means of masses certified to within 0.001 g. This gives rise to extreme accuracy of the calibration points.

The principle consists of reading the raw values recorded by the sensor when masses are applied with a known value. In order to establish this curve, it is advantageously necessary to delete any previous calibrations so that the grip displays the raw values recorded by the sensor.

This calibration curve is defined by measuring five calibration points: $X0$, $Y0$; $X1$, $Y1$; $X2$, $Y2$; $X3$, $Y3$; $X4$, $Y4$.

For each known mass applied to the grip, the uncorrected raw measurement of the sensor $0b$ to $4b$ displayed on the screen is recorded and corresponds to the coordinate X ($X0$ to $X4$). The known true measurement of the mass applied corresponds to the coordinate Y ($Y0$ to $Y4$). In FIG. 3, the value X corresponds to a value recorded by the sensor at a given mass. The projection onto the calibration curve in a solid line makes it possible to obtain the value Y, which is the value displayed by the sensor after calibration.

The five calibration points measured are then used to establish one curve per segment. On each segment, for a value of X recorded by the sensor, there corresponds a corrected value close to the reference values.

Once this calibration curve is established and recorded by the data processing system, when an unknown mass Z is applied to the grip, the sensor records a raw measurement $X_Z$, which is corrected according to the segment on which it is situated in accordance with the formula $Y'=a\,X'+b$. The measurement displayed by the display means 8 is then the coordinate $Y_Z$, which corresponds to the corrected measurement of the mass Z. The point Zc is the measurement point after calibration, whereas the point Zb corresponds to a raw measurement. The ordinate $Y_Z$ of the point Zc therefore corresponds to a corrected measurement, that is to say a calibrated measurement.

In a variant, the calibration points 0 to 4 are imposed at 0 N and 890 N. The choice of the calibration points 1, 2 and 3 must be made carefully according to the range of use of the grip.

It is recommended choosing the points 100, 300 and 500 N for an adult grip and 100, 200 and 300 N for a child grip.

In practice the calibration procedure is as follows:

after the launch of the acquisition software and the deletion of any previous calibration, the width of the grip is adjusted, preferably on an intermediate notch. The grip is then put in calibration mode.

A "0" calibration point is preferably the measurement of the sensor when the grip is placed flat without load. For the other points the grip is suspended from a horizontal fixed bar by means of two straps. In a variant, a ring can be provided in the structure of the grip in which a hook is inserted for suspension of the grip.

Preferably, it is checked that the longitudinal axis of the grip is vertical, by means of a spirit level.

A second "0" calibration point is recorded when the grip is suspended. Three other calibration points are chosen with corresponding masses.

All the measurements obtained are associated with an abscissa X and the real values are associated with an ordinate Y. In this way a calibration curve is obtained that is linear by segments.

It is also possible to check that the values supplied by the grip are accurate. For this purpose standard weights of known mass are applied to the grip and the reference values are compared with the values displayed by the grip.

To do this the steps disclosed previously are carried out again on a sensor calibrated with standard masses of 500 g to 60 kg. Once the measurements are recorded, the force values with "grip flat" are calculated in accordance with the following formula:

Measurement with grip flat×kg=measurement with grip suspended×kg−measurement with grip suspended 0 kg+measurement with grip flat 0 kg.

The values obtained are then compared with the reference values.

If the measurement delivered by the sensor is not substantially linear or if it exhibits a slight difference with respect to the reference values, it is then necessary to carry out a new calibration of the grip.

Use of the system according to the invention has made it possible to determine substantially exactly the change in muscular conditions of certain patients. By way of illustration, results proving the performances of the device were obtained with patients suffering from Duchenne muscular dystrophy or spinal amyotrophy for which maximum gripping forces of less than a few hundreds of grams were able to be recorded. Furthermore, the repeatability of the measurements was proved in several populations of adults and children, healthy or ill.

Numerous combinations can be envisaged without departing from the scope of the invention; a person skilled in the art would choose one or another according to economic, ergonomic, dimensional or other constraints that he will have to comply with.

The invention claimed is:

1. System for measuring a palmar gripping force, comprising a device for measuring said palmar gripping force that comprises:
    a grip comprising an external frame and configured so as to receive a palmar griping force,
    a force sensor configured so as to measure said palmar gripping force,
    a spindle that attaches the force sensor to the external frame,
    an electronic module integrated in the device and comprising at least one microcontroller connected to the sensor for processing data issuing from said sensor,
    wherein the system comprises a strain gauge for detecting forces and from a zero value, and which has a precision at a minimum of 50 g for a range of measurements ranging from 0 to 90 kg, and/or a sensitivity of less than 10 g,
    and the electronic module comprises means for performing the following actions:
    (a)—calibrating the sensor, in which:
    (a1)—the sensor receives a plurality of calibration forces,
    (a2)—establishing a linear calibration function from calibration points, a first coordinate of which is a sensor measurement and a second coordinate of which is the value of said calibration force, said calibration function being linear by segments, and
    (b)—recording a palmar gripping force value according to a first coordinate of a point of the linear calibration function, and determining a calibrated force value corresponding to the second coordinate of said point of the linear calibration function.

2. Measuring system according to claim 1, wherein the electronic module comprises means for transmitting said calibrated force value to at least one of a display unit, a storage unit or a data processing unit.

3. Measuring system according to claim 2, wherein the at least one of the display unit, the storage unit or the processing unit are provided in the electronic module of the measuring device.

4. Measuring system according to claim 2, wherein the at least one of the display unit, the storage unit or the processing unit are provided in a specific module connected to said electronic module of the measuring device, said transmission being at least one of wired or wireless.

5. Measuring system according to claim 1, wherein the calibration of the sensor is done over at least three calibration measurements.

6. Measuring system according to claim 1, wherein at least one internal bar parallel to a first element of the external frame is configured to move in translation towards said first element of the external frame, and the force sensor is configured to measure a force associated with said translation.

7. Measuring system according to claim 6, wherein the grip comprises a means of adjusting an initial separation between the movable at least one internal bar and the first element of the external frame.

8. Measuring system according to claim 1, further comprising means for selecting an operating mode chosen from:
    a so-called measuring mode for said measurement of a palmar gripping force, or
    a so-called calibration mode for implementing said calibration.

9. Measuring system according to claim 1, further comprising means of at least one wired or wireless connection to a control unit.

10. Computer program product that can be loaded into a memory of at least one of a computer or the at least one microcontroller of the electronic module of the measuring system according to claim 1, comprising computer-readable instructions for performing calibration and measuring steps of said measuring system.

* * * * *